United States Patent
Enarson

[11] Patent Number: 6,151,957
[45] Date of Patent: Nov. 28, 2000

[54] MEASURING DEVICE COMPRISING AN EXCITABLE FREQUENCY GAUGE

[75] Inventor: Knut Enarson, Säffle, Sweden

[73] Assignee: Knut Enarson AB, Sweden

[21] Appl. No.: 09/194,169

[22] PCT Filed: May 5, 1997

[86] PCT No.: PCT/SE97/00745

§ 371 Date: Jan. 20, 1999

§ 102(e) Date: Jan. 20, 1999

[87] PCT Pub. No.: WO97/44647

PCT Pub. Date: Nov. 27, 1997

[30] Foreign Application Priority Data

May 22, 1996 [SE] Sweden ............................. 9601876

[51] Int. Cl.[7] .......................... G01N 11/02; G01N 11/16
[52] U.S. Cl. ................. 73/54.28; 73/54.32; 73/53.03
[58] Field of Search ............................... 73/54.28, 54.31, 73/53.04, 53.03, 54.32

[56] References Cited

U.S. PATENT DOCUMENTS

| | | | |
|---|---|---|---|
| 722,576 | 3/1903 | Grand | 73/54.28 |
| 2,807,160 | 9/1957 | Asbeck | 73/60 |
| 3,126,735 | 3/1964 | Vögttle et al. | 73/59 |
| 3,181,349 | 5/1965 | Jansson | 73/59 |
| 3,239,325 | 3/1966 | Roberson et al. | 65/162 |
| 3,285,058 | 11/1966 | Ostroot | 73/59 |
| 3,290,930 | 12/1966 | Drinkwater | 73/136 |
| 3,722,262 | 3/1973 | Gilinson, Jr. et al. | 73/59 |
| 4,129,031 | 12/1978 | Tehon et al. | 73/32 A |
| 4,175,425 | 11/1979 | Brookfield | 73/59 |
| 5,301,541 | 4/1994 | Joseph et al. | 73/54.32 |
| 5,677,481 | 10/1997 | Brown et al. | 73/54.28 |
| 5,948,970 | 9/1999 | Te'eni | 73/54.03 |

FOREIGN PATENT DOCUMENTS

| | | |
|---|---|---|
| 0 071 387 | 2/1983 | European Pat. Off. |
| 380899 | 11/1975 | Sweden |
| 1308416 | 2/1973 | United Kingdom |
| WO91/04480 | 4/1991 | WIPO |

*Primary Examiner*—Hezron Williams
*Assistant Examiner*—David J. Wiggins
*Attorney, Agent, or Firm*—Akerman Senterfitt

[57] ABSTRACT

A device for measuring a parameter such as the mass concentration or the viscosity of a fluid medium such as a suspension or a liquid, including a rotor for rotation in the medium, a drive motor, a drive transmission with a drive shaft for the rotor, and a sensor device for sensing the torque which is transmitted to the rotor and which represents the parameter. The device is distinguished by that the sensor device includes an excitable frequency gauge which is deformed by the torque, and the prevailing natural frequency of which his dependent on the deformation and directly detectable by a stationary detector, which is placed outside the transmission.

11 Claims, 3 Drawing Sheets

MEASURING DEVICE COMPRISING AN EXCITABLE FREQUENCY GAUGE

FIELD OF THE INVENTION

This invention concerns a device according to the preamble of claim 1.

BACKGROUND OF THE INVENTION

Such devices are previously known and are applied in different areas of technology. It is thus previously known to measure the mass concentration in a paper pulp suspension by measuring a resisting torque when rotating a sensor in the suspension to be investigated. The measured torque is based on the force exerted by the rotating body for separating fibres in the suspension. The force and thus the torque thus depends of the quantity of fibres in the suspension. It is further previously known to avoid stuff box friction etc. by leading the rotating shaft which transmits the torque through a hollow shaft and use a sensor functioning according to the principle of equilibrium of forces. This principle is based on the fact that because of an exerted torque, a displacement will occur between the transmitting shaft and the hollow shaft which displacement may be detected. Known measuring methods suffer however from disadvantages with respect to errors in measurement, i. a. due to the connection between the sensor shaft and the hollow shaft. Also in other respects the known measuring methods are unreliable.

It should be noted that the consequences of measurement errors can be substantial. As an example in paper manufacture, if a paper pulp suspension is to be investigated, the economically acceptable concentration interval ranges in a variation of dry contents of only about one percent. Too low concentration may lead to breakage of the resulting paper web, too high concentration results in waste of fibre and too thick paper.

SUMMARY OF THE INVENTION

It is an aim of this invention to eliminate the disadvantages of the previously known solutions and to provide a reliable, accurate economic solution.

This aim is obtained in a device according to the above by the features of the characterizing portion of claim 1.

Hereby it is achieved that the oscillating frequency of a related element, the frequency of which being representative of the torque, is directly detectable by a detector which is placed outside the transmission, which considerably enhances the accuracy as well as the reliability of the device. This firstly because a frequency transmitting element is employed in the sensor device with a minimum of sources of error, and secondly because a frequency signal, which is transmitted from the detector, is considerably more unsensitive to different types of disturbances than is the case of an analog signal. The advantages of using a frequency signal is i.a. that such a signal is uninfluenced by electrical fields around for example electrical power cables which often are located in proximity to the signal cable.

U.S. Pat. No. 3,290,930 is mentioned as an example of comparison wherein, however, a frequency signal which characterizes the torque is transmitted with the aid of a radio transmitter-receiver. Also SE-D-380 899 concerns the use of frequency signals wherein however, this document concerns electronic monitoring of these frequency signals and thus not the location of the detector. In a device according to this invention there are no electrical signals transmitted from the moving parts.

By the sensor device comprising a ring-shaped element carrying a frequency gauge a preferred fastening thereof is obtained.

The features of the claims 3–6 concerns preferred features with respect to the location of the elements of the sensor device.

The claims 9 and 10 concerns preferred locations of the frequency gauge. In that regard, the frequency gauge can be band-shaped. The frequency gauge can also be curved between its ends, which can be fixed.

Further advantages are obtained according to the other claims.

BRIEF DESCRIPTION OF THE DRAWINGS

The invention will no be described in greater detail with reference to the accompanying drawings, wherein.

DETAILED DESCRIPTION OF THE PREFERRED EMBODIMENTS

Figure 1:
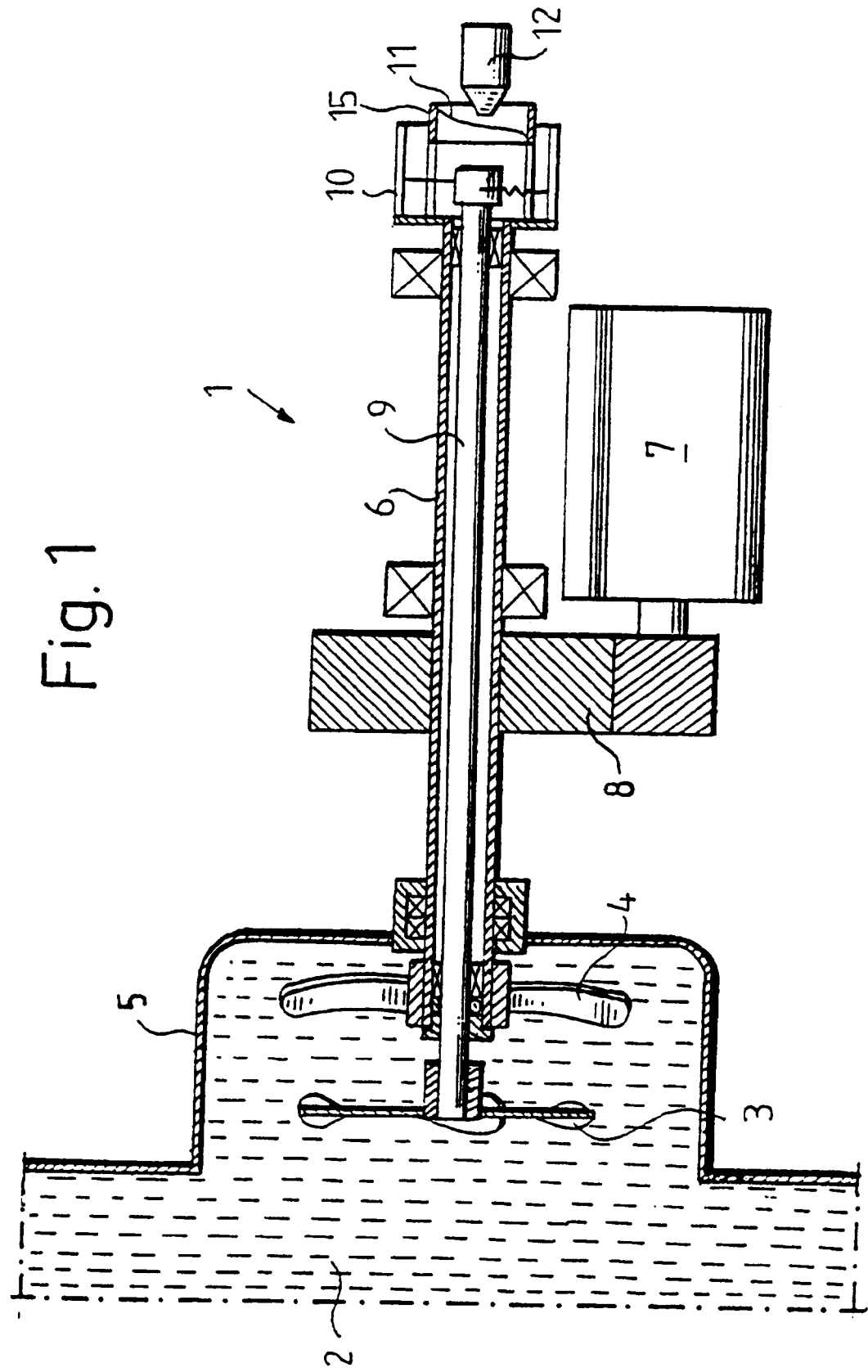
FIG. 1 diagrammatically shows a measuring device according to the invention.

The measuring device of FIG. 1 includes a measuring house 5, which is attached to a conduit for the fluid medium 2 to be investigated, said house 5 comprising a convex bulge on said conduit. A rotor 3 is located inside the measuring housing 5 so as to function as a sensor element. A stirring element 4 which uses propeller action ensures a continuous inflow of the suspension which at the prevailing instant passes the measuring housing and is intended to be measured to the area of the rotor 3. The rotor 3 as well as the stirring element 4 are driven by a motor 7 via a hollow shaft 6, which is directly connected to the stirring element, said hollow shaft having a transmitting connection 8 to the motor 7 as well as with the rotor shaft 9. Axially opposite the location of the rotor 6 the transmission comprises a resilient element (not shown) which allows a rotational displacement between the hollow shaft 6 and the rotor shaft 9 in dependence of the amount of torque being transmitted.

Further the device includes a sensor device 10 with a so called torque meter, which consists of two diagonally acting tension elements which are firmly connected to the part of the transmission which is connected to the hollow axis 6 and which according to the torque depending angular displacement exerts a greater or smaller tension force acting diagonally on a means 15 including a frequency gauge 11. This means (15 in FIG. 2) is fastened to the hollow shaft 9 on a place which is separate from the points of action of said tension elements.

When the transmitted torque varies, a correspondingly varied tension will effect the means 15 and thereby the frequency gauge 11 which thereby will have a different natural frequency of oscillation.

A detector 12 is arranged stationary in the housing of the measuring device 1 and outside the transmission between the motor 7, the rotor 3 and the stirring element 4 and substantially coaxial with said shafts and substantially in line with the frequency gauge 11. Further, in connection with the detector 12 an excitation device is arranged which is adapted to periodically put the frequency gauge 11 in oscillation with its naturally frequency. The detector periodically reads the natural frequency which depends on the load. It should be noted that the oscillations transmitted from the excitation device itself preferably are chosen in such a way that they are not within the natural frequency range of the element 11 and thereby do not disturb the measuring.

In use of the device according to FIG. 1 the rotor 3 will rotate in an environment consisting of representative portion of the fluid medium 2 to be investigated, whereby changes in the mass concentration of the suspension result in a corresponding change of torque. Accordingly the sensor device 10 will effect the means 15 and thereby the frequency gauge 11, which when excited will be put in oscillation with a frequency which is representative of the current situation in the measuring housing 5. The frequency is then detected through a detector 12 which transmits a signal to a Distributed Control System (DCS) and/or a display and so on for further treatment of the received signal and possibly display thereof. This way a measurement of the mass concentration in the conduit is obtained.

Figure 2A:
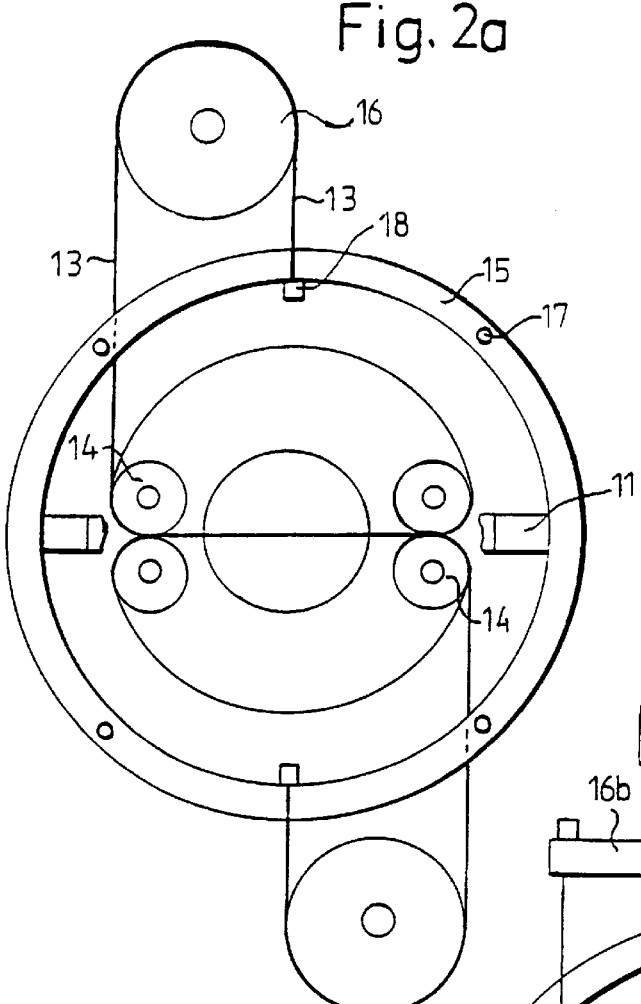
FIG. 2a shows a section of a device according to the invention in the area of the sensor device.

FIG. 2a shows a detail of the sensor device as seen in an axial direction, wherein 13 indicates tensioning wires or threads comprising said tensioning means, and 14 guide rollers for said threats. Each thread is placed helically (see FIG. 3) over outer rollers 16 and attached to the means 15 at diametrically separated fastening points 18. The ring shape means 15, as seen in an axial direction, diagonally carries a frequency gauge which is comprised of thin metal band 11. 17 indicates the bearing points of the ring.

Figure 2B:
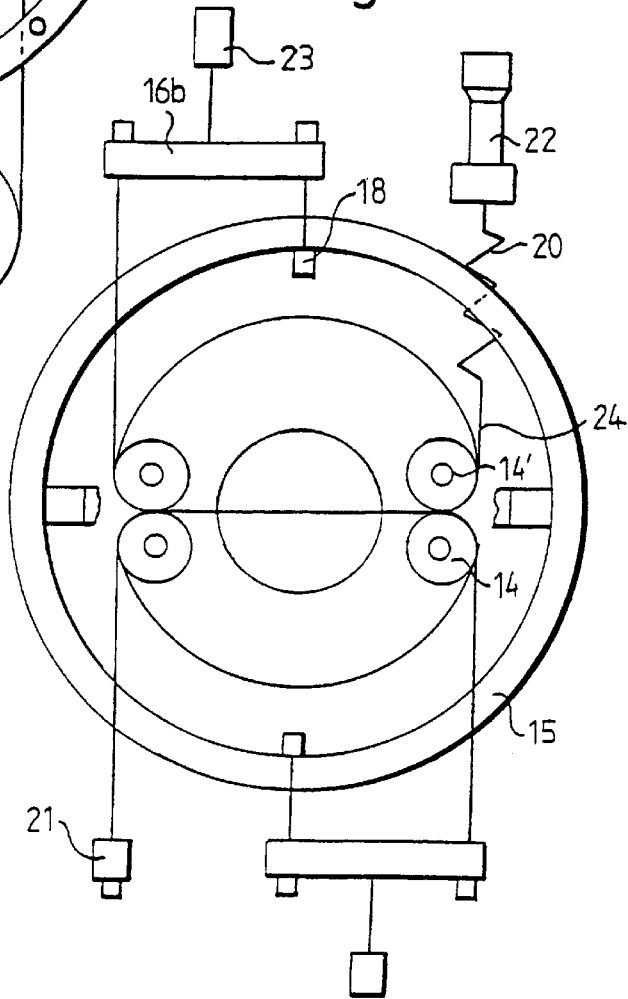
FIG. 2b shows an alternative construction of the device according to the invention.

FIG. 2b shows an alternative construction of the sensor device, where the outer rollers 16 of FIG. 2a are replaced with a cradle 16b having a thin band pivotally fastened in a console 23. Further, a device for pretensioning the force on the means 15 is shown, including a resilient means 20, a tensioning device 22 and a tensioning wire 24 coming from these elements, which over guide rollers 14', which are coupled to the rotor shaft, are led to a fastening point 21. This pretension arrangement results in a torque which is directed opposite to the torque emanating from the functional rotor. With adjusted tensioning of the resilient means 20, a chosen initial relative rotation between the hollow shaft and the rotor shaft is obtained, giving the possibility of variation of the deformation of the frequency gauge. This way a desired zero frequency may be set. The tensioning device of this kind may of course be used also in connection with the device according to FIG. 2a and it may also be left out from the device according to FIG. 2b.

In this connection it may be mentioned that the calibration over the measurement range is easily obtained by testing in a test rig, although fine calibration should be undertaken with the selected rotor in the functional environment. In order to obtain sufficient sensitivity, the means cooperating with the frequency gauge, e.g. 15, are dimensioned in such a way that a sufficiently great frequency variation is obtained in the actual measuring range.

Figure 3:
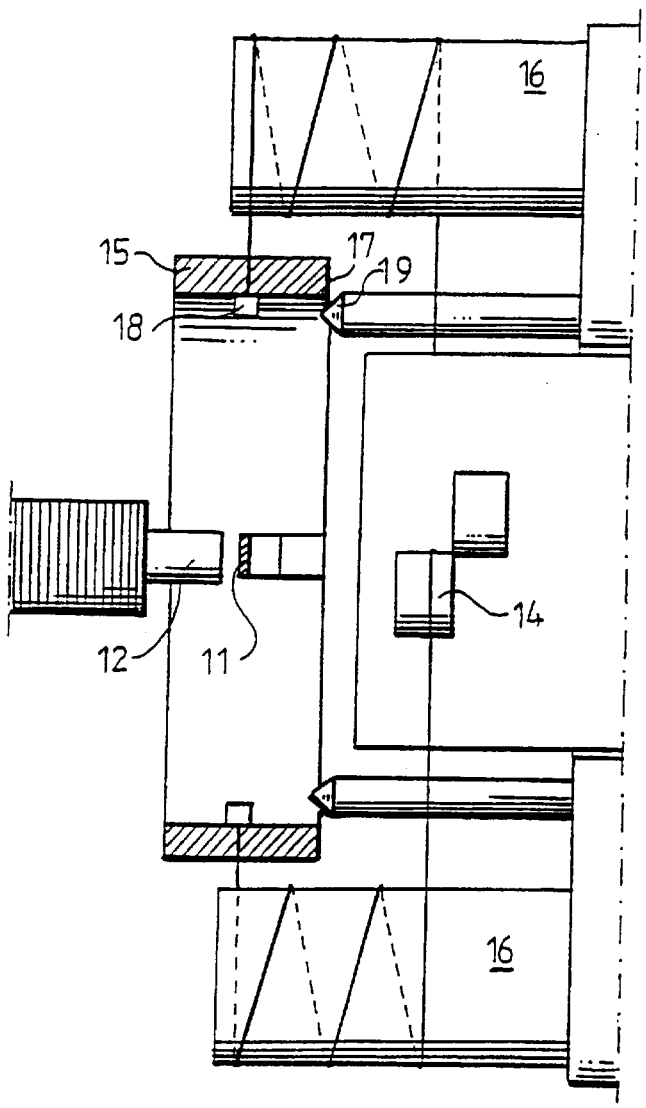
FIG. 3 shows the device according to FIG. 2a in an axial section.

FIG. 3 thus shows a device according to FIG. 2a in an axial section, whereby the ring shaped means 15 is fastened to a plate being connected to the hollow shaft over sharp conical bearing pins 19 which carries the means 15 in the recesses 17, symmetrically with respect to the points of action of the force and the fastening points of the element 11. In the embodiment shown in FIG. 2a and 3, the ring is so small that it is placed axially outside the torque shaft.

The detector 12 indicates a combined detector/excitation device which on the one hand can excite the element 11 with a chosen frequency and on the other hand can detect the prevailing natural frequency of frequency guage 11. The unit 12 may for example be comprised of a simple coil or transformer having an iron core.

Figure 4:
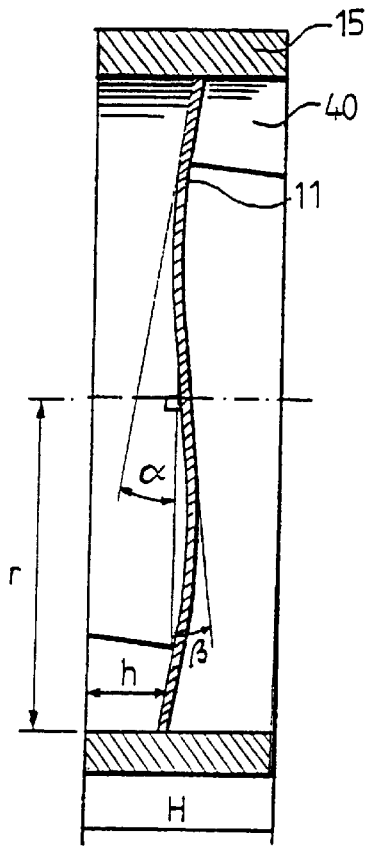
FIG. 4 shows a detail of the sensor device according to the invention.

FIG. 4 shows diagrammatically the ring-shaped means 15 with the frequency gauge 11 disposed in a curved configuration which is preferred since this placing of the element, or the band 11, gives the band an inherent tension, and therefore no pretension of the element is necessary when it is mounted in the means 15. In many applications it is desired to have the possibility of arranging the detector as close to the frequency gauge as possible. This is most simply achieved by having the element 11 disposed at an almost right angle to the axis of the means 15 (the rotational axis) in the area of said axis. By choice of the end angle $\alpha$ of the element and a suitable relationship h/H/r, the angle $\beta$ may be minimized. 40 indicates fastening notches for the band 11. Fastening of the band as well as notches are suitably obtained by soldering.

As is indicated above the device is adaptable also for measuring other parameters, as for example the viscosity of a liquid. Also other placing arrangements of the sensor device is possible and other types of holding means corresponding to the ring-shaped means 15 may come in question. It is also possible to use other kinds of frequency gauges as for example threads and also an entirely straight disposition such as rods, bars, grooves or strips is possible, although, as is mentioned above, the curved configuration according to the Figures is preferred.

Also other kinds of detectors may be used, for example Hall detectors and also laser detectors. The excitation device may also be comprised of a separate unit which is placed in proximity to the detector. In some applications of the invention a disposition of the rotor shaft in a hollow shaft is not necessary, but in connection with the shown arrangement, i.e. measuring the mass concentration in a paper pulp suspension, the arrangement inside the hollow axle, in a per se known manner, is highly preferred since error in measurement due to stuff box friction etc are substantially eliminated. It may be noted that the use of a torque meter is not limited to the shown embodiment including a rotor shaft disposed inside a hollow shaft.

The means 15 may be comprised of an element transmitting the torque or being connected to a part of the transmission wherein the transmitted torque is effecting the ring and thereby also effecting the element 11 directly or indirectly. The means 15 may be comprised of a ring-shaped means, and the ring may have such great dimensions that it surrounds the torque shaft and the rollers may find their places between the ring and the shaft and this way it is substantially avoided that the ring is affected by sideward directed forces.

A resilient means being disposed between the rotor shaft and the hollow shaft may also be constructed as a resilient sealing means placed at the end of the rotor.

As is indicated above the frequency gauge may be carried otherwise than through a ring shaped means as long as it emits a frequency signal which represents the transmitted torque.

What is claimed is:

1. A device for measuring a parameter such as the mass concentration or the viscosity of a fluid medium such as a suspension or a liquid, including a rotor driven by control means for rotation in said medium under a reactive counter-torque due to the viscous effect of said suspension or liquid, a drive motor, a drive transmission with a drive shaft for the rotor, and a sensor device for sensing a torque which is transmitted to the rotor and which represents said parameter, wherein the sensor device comprises an excitable frequency gauge which is deformed by said torque to generate an output signal of a natural prevailing frequency dependent on said torque, and wherein the prevailing natural frequency is dependent on a deformation and is directly detectable by a stationary detector located outside the drive transmission.

2. The device according to claim 1 having an axial direction and a lateral direction, wherein:

the sensor device has a ring-shaped means which is included in the transmission, and wherein said ring-shaped means is essentially mounted diagonally across the device, as seen in the axial direction, and carries the frequency gauge.

3. The device according to claim 1, wherein the transmission comprises a plurality of shaft parts with a portion which includes a resilient element allowing relative rotation between the shaft parts, said shaft parts located at each side of the portion as a function of the prevailing torque, whereby the frequency gauge is connected to each part of the transmission in link-wise combination with a torque meter.

4. The device according to claim 2, wherein the ring-shaped means is arranged essentially coaxially with the rotor shaft.

5. The device according to claim 4, wherein the ring-shaped means is located in a position of the rotor shaft axially opposite the rotor.

6. The device according to claim 1, wherein the detector is coaxial with the rotor.

7. The device according to claim 1, further comprising at least one of an electronic or electromagnetic exciting means for exciting the frequency gauge.

8. The device according to claim 7, wherein the detector and the exciting means are an integrated unit.

9. The device according to claim 1, wherein the frequency gauge is band-shaped.

10. The device according to claim 1, wherein the frequency gauge is curved between its ends, and said ends are fixed in position on the device.

11. The device according to claim 10, wherein the frequency gauge element is disposed in such a way that it extends essentially at a right angle to the rotational axis in the area of attachment along this axis of the fluid measuring device.

* * * * *